United States Patent [19]

Carnahan

[11] Patent Number: 4,778,998
[45] Date of Patent: Oct. 18, 1988

[54] HUMIDITY COMPENSATION FOR A PHOTOIONIZATION TYPE DETECTOR

[75] Inventor: Byron L. Carnahan, Sewickley, Pa.

[73] Assignee: Mine Safety Appliances Company, Pittsburgh, Pa.

[21] Appl. No.: 58,813

[22] Filed: Jun. 5, 1987

[51] Int. Cl.⁴ .............................................. G01T 1/18
[52] U.S. Cl. ................................. 250/382; 250/423 P
[58] Field of Search ............... 324/464; 250/252.1 A, 250/308, 358, 372, 373, 423 P

[56] References Cited

U.S. PATENT DOCUMENTS 4,429,228  1/1984  Anderson .......................... 250/374
4,698,314  10/1987  Tao .............................. 250/423 P X Primary Examiner—Eugene R. Laroche
Assistant Examiner—Steven J. Mottola
Attorney, Agent, or Firm—Reed Smith Shaw & McClay

[57] ABSTRACT

A photoionization type detector utilizes a photoionization sensor to detect the concentration of contaminants in the air, a humidity sensor to detect the water vapor concentration in the air and a temperature sensor to detect the temperature of the air. A microcomputer first calculates the water vapor concentration present in the air from the humidity and temperature sensor readings. Then, the microcomputer applies a predetermined correction factor corresponding to the calculated absolute humidity to the response of the photoionization sensor. This correction factor compensates for the negative cross-sensitivity of the photoionization sensor the humidity in the art and produces an accurate contaminant concentration level which is then displayed.

13 Claims, 2 Drawing Sheets

HUMIDITY COMPENSATION FOR A PHOTOIONIZATION TYPE DETECTOR

FIELD OF THE INVENTION

The present invention relates to photoionization type detectors. More specifically, the present invention relates to photoionization type detectors which have a humidity compensation capability.

BACKGROUND OF THE INVENTION

Photoionization gas detection is commonly used in applications where dangerous gases may infiltrate the breathing environment. A serious drawback to the implementation of photoionization gas detection in a portable instrument is the large degree of negative cross sensitivity exhibited by such sensors to water vapor. For example, the studies of Chilton, et al., *American Industrial Hygiene Association Journal*, 44:710 through 715 (1983), Barski, et al., *American Industrial Hygiene Association Journal*, 46:9–14 (1985) confirm that the response of a photoionization detector is markedly reduced with increased water vapor concentration.

In typical operation, a portable instrument using a photoionizing detector is calibrated prior to use with a span gas containing a known concentration of an ionizeable species, and a fixed, normally near zero partial pressure of water vapor. If such an instrument is subsequently used to sample an ambient atmosphere containing the same contaminant at the same concentration level, the instrument will invariably register a value lower than the calibration reading due to the presence of water vapor in the field sample. As the ambient atmosphere always contains some degree of humidification, in actual operation instruments of this type are susceptible to gross underestimations of the toxicity level of the surrounding breathing environment.

SUMMARY OF THE INVENTION

Accordingly, one object of the present invention is to provide a photoionization type detector that has the capability of compensating for humidity in the surrounding atmosphere.

Another object of the present invention is to provide a photoionization type detector that has the capability of compensating for the negative cross sensitivity therein due to humidity in the tested atmosphere.

Another object of the present invention is to provide humidity compensation for a photoionization type detector that would be incorporated directly into the instrument so that operator would be free from the need to correlate correction factors with humidity.

These and other objects of the present invention are accomplished with a photoionization type detector with humidity compensation comprising: a photoionization sensor for detecting contaminants in the air and producing a signal proportional to the contaminants sensed; a humidity sensor for detecting the humidity in the air and producing a signal proportional to the humidity sensed; a temperature sensor for detecting the temperature of the air and producing a signal proportional to the temperature sensed; a microcomputer connected to receive as inputs, the outputs of the photoionization sensor, humidity sensor and temperature sensor for calculating the absolute water vapor concentration of the sampled atmosphere from which the microcomputer then chooses a predetermined correction factor and applies the correction factor to the photoionization sensor signal to compensate for negative cross sensitivity therein due to the humidity; and display means connected to the microcomputer for showing the compensated signal.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawing, wherein.

DESCRIPTION OF THE PREFERRED EMBODIMENT

Figure 1:
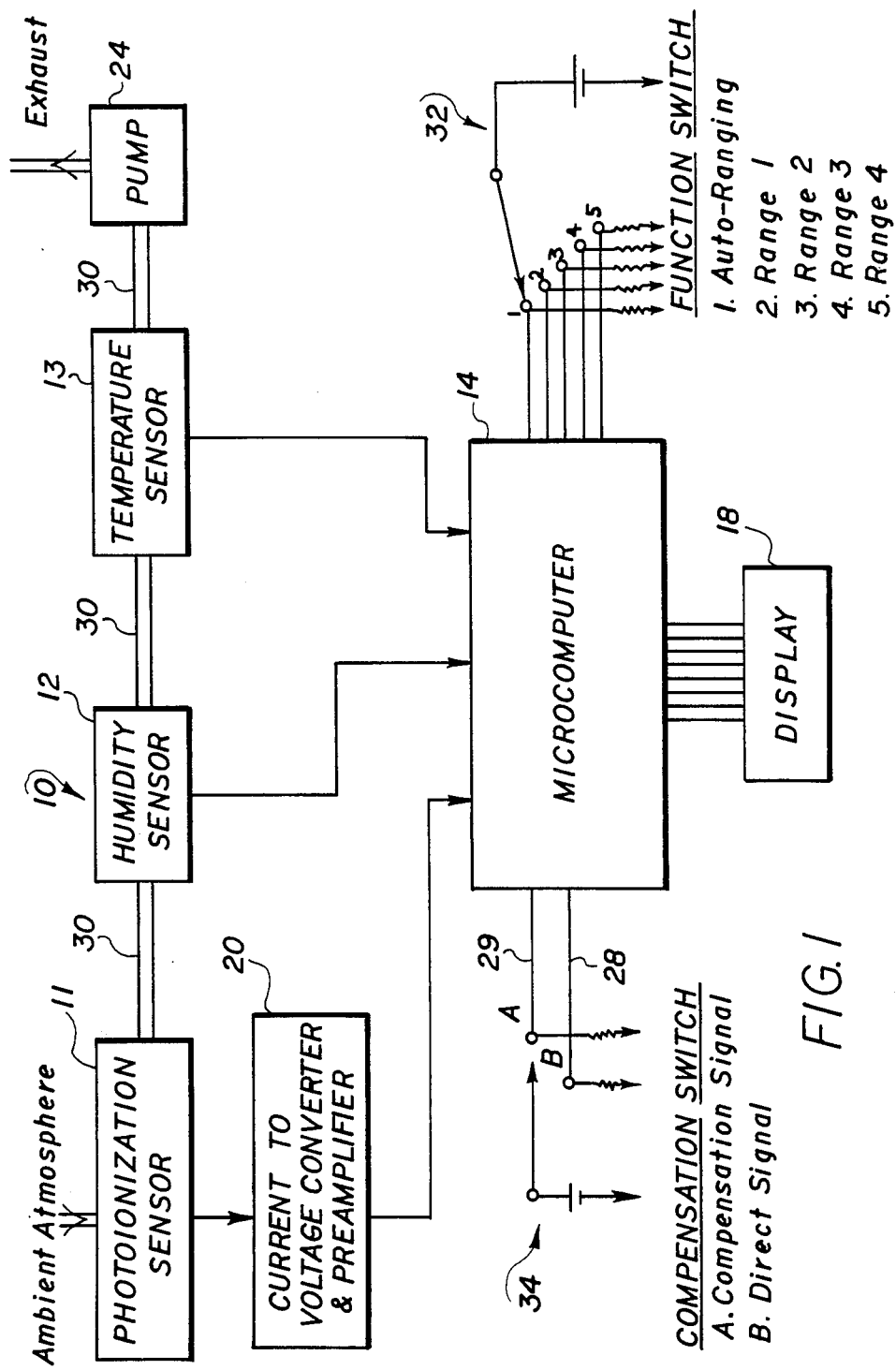
FIG. 1 is a block diagram of the photoionization type detector with humidity compensation.

Referring now to the drawings, wherein like reference numerals designate identical or corresponding parts throughout the several views, and more particularly FIG. 1 thereof, there is shown a photionization type detector with humidity compensation 10. The photoionization type detector with humidity compensation 10 is comprised of a photoionization sensor 11 that senses contaminant gases, such as benzene, in the surrounding atmosphere, a humidity sensor 12 which detects the humidity of the atmosphere analyzed by the sensor 11, and a temperature sensor 13 which detects the temperature of the atmosphere analyzed by the sensor 11. The humidity and temperature sensed by the humidity sensor 12 and temperature sensor 13, respectively, causes electric signals to be produced therefrom corresponding to the humidity and temperature of the air. These signals pass to a microcomputer 14 which computes the absolute degree of humidification of the analyzed atmosphere and uses this value to modify the photoionization sensor 11 signal according to a predefined value to compensate for the negative cross sensitivity in the photoionization sensor 11 due to the humidity of the analyzed atmosphere. The resulting signal from the microcomputer 14 is an essentially accurate signal with respect to the concentration of detected contaminant in the atmosphere. A display 18 shows the compensated signal to a viewer.

Figure 2:
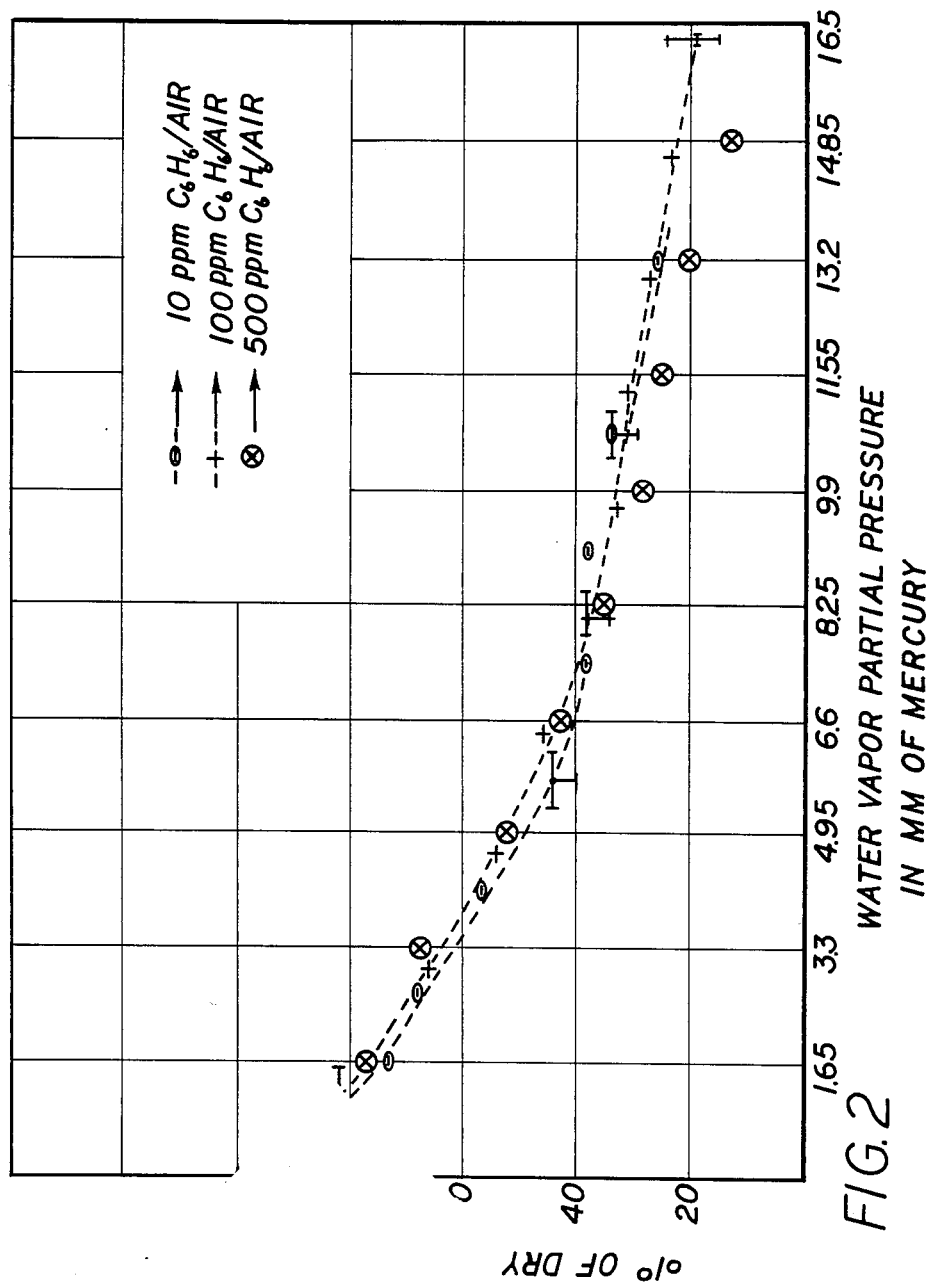
FIG. 2 is a graph of the response of a photoionization detector for several different concentrations of a gas showing the photoionization sensor signal normalized to its dry air response as a function of the partial pressure of water vapor in the sampled atmosphere.

More specifically, the photoionization type detector with humidity compensation is based on the discovery that for a given contaminant gas, for example benzene, the decrease in detector response as a function of water vapor concentration is independent of the contaminant level concentration over a wide range of contaminant concentration levels. Thus, in a sampling situation, the water vapor concentration can be determined, and a predetermined factor can be applied to the response of the photoionization sensor which would correct the humidity compromised measurements to the values which would be obtained under calibration, i.e., dry air conditions. This phenomena is evidenced in FIG. 2 wherein there is a graph of three different concentrations of, for example, benzene in air that are plotted on a graph of percent dry air signal versus relative humidity. The Y axis of the graph is the percent signal response of the sensor 11 relative to dry air. The X axis of the detector is the partial pressure of water vapor in the air. The graph shows that, as the humidity increases in the air being sensed, the accuracy of the response of the photoionization sensor 11 decreases. With a partial pressure of water vapor at only 5 mm of mercury (which for the conditions present at the time of measurement represented a relative humidity of 25% RH) present in the air being sampled, the response of the photoionization sensor 11 is approximately 50% below what the actual response should be. In an environment where toxic gases are present and the photoionization sensor is relied upon to inform users of the toxicity of the atmosphere, this error could place the operator's safety in jeopardy. Furthermore, the graph also shows that for three different concentrations of benzene in air, the response of the photoionization sensor 11 as a function of relative humidity is essentially identical. This indicates that the decrease in detector response as a function of water vapor concentration is independent of the contaminant level concentration over a wide range of contaminant concentration levels. By multiplying the response of the photoionization sensor 11 by the inverse of the Y value of the curve corresponding to the absolute humidity derived by the microcomputer 14 from the signals provided by the humidity sensor 12 and the temperature sensor 13, an accurate determination of the concentration of a detected gas can be obtained. For instance, referring to FIG. 2, if the water vapor partial pressure of the sensed air is 10 mm of mercury, the corresponding Y value of the curve is 33% or one-third of the dry air response. By multiplying the response of the photoionization sensor 11 by a factor of three, $1 + \frac{2}{3}$(the inverse of Y), the accurate response of the photoionization sensor 11 is obtained. The experiment carried out to obtain FIG. 2 utilized the blending of a stream of air having a known concentration of contaminant with a second air flow having a known humidity. Briefly, the gas blending apparatus utilized three different supply channels, with one channel having a known concentration of test gas in air, the second channel having a known partial pressure of water vapor in air and the third channel being dry air. The humidity in the second channel was obtained by passing a dry air stream supply therein through a bubbler. The three channels were then combined to achieve the desired concentration of test gas with a desired humidity. See, Chilton, et al., supra, for a complete description of gas blending experimentation. The experiment to obtain the data exhibited by FIG. 2 is carrie out at approximately 22° C.

In a preferred embodiment of many possible embodiments, a photoionization sensor 10, which is well known in the art continuously senses the surrounding atmosphere for harmful gases. At the same time a humidity sensor 12, such as a Mepco/Electra Relative Humidity Sensor, part number 5X38H122R, continually senses the same atmosphere that is analyzed by the photoionization sensor 11. This sensor is a capacitor, the value of which depends on the relative humidity. As the microcomputer 14 input requires a voltage signal, the humidity sensor's capacitance must be converted to a voltage signal. This can be done in a number of ways, one of which was described by Kurt Irgum in Analytical Chemistry, Vol. 55, 1983, pages 1186–1187. The humidity sensing is accomplished by placing the humidity sensor 12 downstream in air channel 30 of photoionization sensor 10. Ambient atmosphere is continually passed through the photoionization sensor 11 and the humidity sensor 12 via air channel 30 by a pump 24. A pump 24 that can be used is MSA Model B Pump assembly and motor. Similarly, a temperature sensor 13 is placed downstream of humidity sensor 12 in the air channel 30 to detect the temperature of the analyzed atmosphere. A temperature sensor could, for example, be a National Semiconductor Model LM335 Precision Temperature Sensor applied as per the Calibrated Sensor described in the National Semiconductor Data Conversion/Acquisition Databook, 1984 Edition, pages 9–17. The response of the humidity sensor 12 and the temperature sensor 13 is fed into a microcomputer 14. Microcomputer 14, for example a Motorola MC68H811DY HCMOS Single-Chip Microcomputer, receives as input the responses of the photoionization sensor 11, the humidity sensor 12 and the temperature sensor 13. Depending on the setting of a function switch 32, the signal from the photoionization sensor is either processed by the microcomputer on one of the manually selected ranges of concentration of contaminant in air or, if the switch is in the autorange setting, the microcomputer automatically processes the signal on the appropriate range, as is well known in the art.

From the humidity and temperature sensors the microcomputer 14 calculates the water vapor concentration in the sample stream drawn from the ambient atmosphere. This is accomplished from the definition of relative humidity $$P_w = (H_R/100) * P_s \tag{1}$$

where Pw is the partial pressure of water in mm of mercury at temperature T in °C., Ps is the partial pressure of water in mm of mercury for complete saturation at temperature T, and $H_R$ is the relative humidity in percent. The partial pressure Ps is $$P_s = 10 + [(8.1076 - 1750.3/(235+T)]\tag{2}$$

substituting equation 2 into equation yields $$P_w = (H_R/100) * [10 + (8.1076 - 1750.3/(235+T)]\tag{3}$$

Here T is measured by the temperature sensor 13 and $H_R$ is measured by the humidity sensor 12.

The microcomputer 14 then uses the value obtained from the calculation of the water vapor concentration to generate a correction factor to be applied to the raw signal from the photoionization sensor 11.

Recalling the procedure described above for determining the correction factor and that Y is the fraction of signal response of the sensor 11 relative to dry air, it has been determined that $$Y = 1.0 e^{-0.12 \times P_w} \tag{4}$$

(on a % basis $$Y = 100\% * e^{-0.12 \times P_w}).$$

The correction factor to apply to the humid air signal is then $$C = (1/Y = 1.0 e^{0.12 \times P_w} \tag{5}$$

If Sm is the signal level in humid air and Sa is the signal level which would be observed if the air were dry, i.e., the actual dry air signal, then $$S = C \times S_m = S_m * e^{0.12 \times P_w} \tag{6}$$

where Pw is defined in equation 3.

It should be noted that the photoionization sensor 11 signal contains information corresponding to current level. The microcomputer requires the input to be voltage dependent. The humidity and temperature sensors, as mentioned above, provide signals already in the proper form. A current-to-voltage converter and preamplifier 20 is used to place the signal from the photoionization sensor 11 in the proper form and is electrically connected between sensor 11 and microcomputer 14. A current-to-voltage converter is a standard electronic subsystem described in numerous publications such as the Burr-Brown Product Data Books, 1982 Edition, pages 1–34.

The correction value can be obtained several ways. One possible way is to store in the memory of the microcomputer 14 each value of the inverse of the curve at a predetermined set of discrete humidity values. When the humidity calculation is completed, the microcomputer 14 can then search its memory for the stored humidity value most closely equal to the calculated value and take the corresponding correction value (the inverse of the Y value at the X or humidity value) identified therewith. Another way to calculate the correction value is to maintain in memory the equation of the curve shown in the graph of FIG. 2. After the humidity or water vapor concentration is determined, the concentration is substituted into the X-variable of the equation, which, in turn, yields the Y value of the curve corresponding to the water vapor concentration. The Y value is then inverted, thus yielding the correction factor.

Depending on the setting of the compensation switch 34, the signal from the photoionization sensor is or is not adjusted by the correction. If the compensation switch 34 is set to channel 28 then the signal from the photoionization sensor 11 is not adjusted by the correction factor. If the compensation switch 34 is set to channel 29 the signal from the photoionization sensor is corrected by the calculated correction factor. The correction is accomplished by the multiplication of the photoionization sensor signal by the correction factor.

The operation of multiplication between the photoionization sensor 11 signal and the correction factor generator 14 is used because the response of the photoionization sensor 11 is a function of the concentration of gas present, but the response of the sensor 11 with regard to the accuracy of the concentration detected is only a function of humidity. Multiplying the response of the photoionization sensor 11 by a predetermined correction value yields the correct result regardless of the concentration of gas. This is in contrast to using, for instance, addition where different correction values have to be determined to compensate correctly for each concentration of gas detected. Thus multiplication saves a step over addition to correctly compensate the photoionization sensor response.

The corrected signal is then delivered, either corrected or uncorrected as determined by the setting of the compensation switch, to a display 18. The display can be, for example, one of a number of liquid crystal display units such as a Modutec Model BL 100.

Obviously, numerous (additional) modifications and variations of the present invention are possible in light of the above teachings. It is therefore to be understood that within the scope of the appended claims, the invention may be practiced otherwise than as specifically described herein.

What is claimed is:

1. A photoionization type detector with humidity compensation comprising:
   a photoionization sensor for detecting contaminants in the air and producing a signal proportional to the contaminants sensed;
   a humidity sensor for detecting the humidity in the air and producing a signal proportional to humidity sensed;
   a temperature sensor for detecting the temperature of the air and producing a signal proportional to the temperature sensed;
   a microcomputer connected to receive as inputs, the outputs of the photoionization sensor, humidity sensor and temperature sensor for calculating the humidity from which the microcomputer then chooses a predetermined correction factor and applies the correction factor to the photoionization sensor signal to compensate for negative cross sensitivity therein due to the humidity; and
   display means connected to the microcomputer for showing the compensated signal.

2. An apparatus as described in claim 1 wherein the correction factor is $1.0e^{+0.12 \times Pw}$ where Pw is the partial pressure of water vapor in mm of mercury.

3. An apparatus as described in claim 2 wherein $$Pw = (H_R/100 * Ps,$$

where $H_R$ is the relative humidity in % and is measured by the humidity sensor, and Ps is the partial pressure of wter in mm of mercury for complete saturation at temperature T.

4. An apparatus as described in claim 3 wherein $$Ps = 10 + [(8.1076 - 1750.3/(235 + T)]$$

where $H_R$ is the relative humidity in % and is measured by the humidity sensor, and T is the temperature in °C. and is measured by the temperature sensor.

5. An apparatus as described in claim 1 wherein there is a current-to-voltage convertor preamplifier electrically connected to and between the photoionization sensor and the microcomputer.

6. An apparatus as described in claim 2 wherein the microcomputer has a combination switch that allows either the compensated signal to pass to the display, or an uncompensated signal to pass to the display, and a function switch that has at least one range for looking at a certain contaminant concentration level.

7. An apparatus as described in claim 6 wherein the microcomputer applies the correction factor to the photoionization sensor signal by multiplying the correction factor thereto.

8. A method for compensating the negative sensitivity due to humidity of a photoionization device comprising the steps of:
   detecting with a photoionization sensor the concentration of contaminants in the surrounding atmosphere;
   detecting the humidity and temperature in the surrounding atmosphere;
   calculating the absolute humidity of the surrounding atmosphere;
   determining a correction factor corresponding to the calculated absolute humidity to compensate for the negative sensitivity of the photoionization sensor; and applying the correction factor to the detected concentration of contaminants to achieve an accurate contaminant concentration level.

9. A method as described in claim 8 wherein the correction factor is $1.0e^{+0.12 \times Pw}$ where Pw is the partial pressure of water vapor in mm of mercury.

10. A method as described in claim 9 wherein $$Pw = (H_R/100) \times Ps.$$

where $H_R$ is the relative humidity in % and is determined in the step of detecting humidity, and Ps is the partial pressure of water in mm of mercury for complete saturation at temperature T.

11. A method as described in claim 10 wherein $$Ps = 10^{+[8.1076 - 1750.3/(235 + T)]}$$

so $$Pw = H_R/100 * (10^{+[8.1076 - 1750.3/(235 + T)]}$$

where $H_R$ is the relative humidity in %, and T is the temperature in °C. with $H_R$ and T being determined in the step of detecting humidity and temperature.

12. A method as described in claim 8 wherein the applying step includes the step of multiplying the detected concentration by the correction factor.

13. A method as described in claim 9 wherein the applying step includes the step of displaying the accurate contaminant concentration level

* * * * *